United States Patent [19]

Nozawa et al.

[11] Patent Number: 4,678,666
[45] Date of Patent: Jul. 7, 1987

[54] TOPICAL ANTI-INFLAMMATORY COMPOSITIONS

[75] Inventors: Shigenori Nozawa; Katsumi Ohaya, both of Aichi; Toshiji Kawazoe, Inuyama, all of Japan

[73] Assignee: Pfizer Inc., New York, N.Y.

[21] Appl. No.: 896,370

[22] Filed: Aug. 14, 1986

Related U.S. Application Data

[63] Continuation of Ser. No. 646,403, Sep. 4, 1984, abandoned, which is a continuation of Ser. No. 509,114, Jun. 29, 1983, abandoned.

[30] Foreign Application Priority Data

Jul. 13, 1982 [JP] Japan ................................ 57-121853

[51] Int. Cl.$^4$ ............................................ A61K 31/78
[52] U.S. Cl. ..................................................... 424/81
[58] Field of Search ............................................ 424/81

[56] References Cited

U.S. PATENT DOCUMENTS 3,591,584  7/1971  Lombardino ....................... 260/243
4,434,164  2/1984  Lombardino ....................... 424/246

FOREIGN PATENT DOCUMENTS 2355510  1/1978  France .

OTHER PUBLICATIONS

P. Schiantarelli et al., "Anti-inflammatory Activity and Bioavailability of Percutaneous Piroxicam", Arzneim-Forsch./Drug Res., 32(I), No. 3, p. 230 (1982).
Chemical Abstracts, vol. 95, p. 103322x (1981).

Primary Examiner—Stanley J. Friedman
Attorney, Agent, or Firm—Charles J. Knuth; Peter C. Richardson

[57] ABSTRACT

A novel formulation of piroxicam for dermatological administration is disclosed. Pharmaceutical compositions containing piroxicam, lower alkanols, water, carboxyvinyl polymer, polyhydric alcohols, alkanolamines and optionally film-forming agents are prepared, said compositions having a pH of from about 6.5 to about 9.0. The novel formulation is characterized by excellent applicability on the skin, skin-permeability and good stability. The novel formulation, which is in gel ointment form, is as effective as orally administered peroxicam and is well suited for topical administration through skin for the treatment of various types of inflammatory conditions.

4 Claims, No Drawings

TOPICAL ANTI-INFLAMMATORY COMPOSITIONS

RELATION APPLICATION

This is a continuation of Ser. No. 646,403, filed Sept. 4, 1984, which in turn is a continuation of Ser. No. 509,114, filed June 29, 1983, both are now abandoned.

BACKGROUND OF THE INVENTION

This invention relates to new and useful anti-inflammatory compositions for topical administration containing as an active ingredient, piroxicam, viz., N-(2-pyridyl)-2-methyl-4-hydroxy-2H-1,2-benzothiazine-3-carboxamide 1,1-dioxide, which is a compound of the formula:

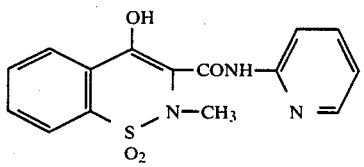

More particularly, this invention relates to certain novel anti-inflammatory pharmaceutical compositions for external use comprising an effective anti-inflammatory amount of piroxicam, nontoxic bases for topical formulation and appropriate solvents therefor.

Piroxicam is a nonsteroidal anti-inflammatory agent described and claimed under its chemical name by J. G. Lombardino in U.S. Pat. No. 3,591,584 and it is highly effective in therapy when administered to mammalian subjects suffering from chronic arthritic rheumatism, arthritis deformans, low back pain, shoulder pain, cerrico-omo-brachial syndrome, trauma or the pain caused by tooth extraction. Piroxicam is sold in capsule form world-wide and it is recognized to be a potent long-acting drug that ensures an effective piroxicam blood level when admininstered orally once a day.

Some of the above diseases require a relatively long period of treatment in order to avoid or minimize side effects, and it would be desirable that the oral administration be replaced by the topical administration as the disease reaches a recuperative stage. Furthermore, the topical administration is suitable for a mild case or a case where the lesion is localized.

This invention is meant to provide anti-inflammatory compositions suitable for topical administration: these compositions are characterized in that they comprise an effective anti-inflammatory amount of piroxicam, nontoxic bases for topical formulation and solvents.

Piroxicam is very active as an anti-inflammatory agent, but it is sparingly soluble in water and is not liposoluble. When piroxicam is simply compounded in suspension with conventional bases for ointment or cream, it is poorly absorbed through skin and does not afford expected therapeutical effects. Additionally, the formulation so produced is very sticky and unpleasant to apply to a wide area of the skin. The active ingredients in the formulation may also be lost easily when in contact with clothing. In this connection, it seems possible to apply piroxicam in the form of a tincture after dissolving same in an alcoholic solvent such as ethanol. However, piroxicam will precipitate on the skin due to the evaporation of the solvent and will not be absorbed through the skin.

A gel ointment is prepared by adding a polymer to a lower alkanol-water system. It is generally a preferred form for topical administration because it is refreshing and not sticky. Unfortunately, the gel ointment cannot be formulated with piroxicam according to the standard techniques since piroxicam is sparingly soluble in water or any other solvent. Piroxicam, in the presence of moisture, turns into a hydrate thereof which is less soluble than piroxicam itself and this hydrate crystallizes out gradually. This not only reduces the absorbability of piroxicam through skin, but also impairs the coating and stability of the gel ointment.

A further problem arises when the gel ointment is applied to the skin in that dermal salt causes crystallization of piroxicam. This hydrate forms a yellow deposit on the skin. The hydrate will also come off when in contact with clothing or other material.

A similar problem arises when the gel ointment is applied directly to sweating skin, viz., a polymer gel-forming agent in the ointment is salted out and, as a result, the ointment agglomerates on the skin instead of forming a film layer. This affords unpleasantness to the user and the active ingredient is lost, whereby poor therapeutic effects are obtained.

SUMMARY OF THE INVENTION

In accordance with the present invention, there has now been developed a novel anti-inflammatory composition for external use that has excellent skin-permeability and none of the defects described above. It has thus been surprisingly found that by combining and blending an effective anti-inflammatory amount of piroxicam with water-soluble bases, solvents, gel-forming agents and, if necessary, an appropriate amount of film-forming agents, one can obtain an anti-inflammatory composition for external use that has an unexpectedly high degree of therapeutic efficacy and good stability. It is, in addition, pleasant to use.

More specifically, there is now provided for the first time an anti-inflammatory composition for external use which comprises piroxicam; a lower alkanol having from one to four carbons; water; a gel-forming amount of carboxyvinyl polymer; one or more polyhydric alcohols selected from the group consisting of a lower alkylene glycol having from two to six carbons, glycerine and polyethylene glycol having an average molecular weight from 200 to 2000; and a piroxicam-solubilizing amount of one or more alkanolamines selected from the group consisting of monoalkanol-amine having from one to four carbons, dialkanol-amine having from two to eight carbons and trialkanolamine having from three to twelve carbons, said composition having a pH range of from about 6.5 to about 9.0.

Also encompassed by this invention is an anti-inflammatory composition for external use which contains in addition to the above-stated ingredients, an effective amount of a film-forming agent selected from the group consisting of carboxymethyl cellulose, hydroxyethyl cellulose and polyvinylpyrrolidone, said composition having a pH range of from about 6.5 to about 9.0.

DETAILED DESCRIPTION OF THE INVENTION

An effective anti-inflammatory amount of piroxicam in the composition is preferably from about 0.3% to about 2.0% by weight, based on the weight of the total. Use of a lower piroxicam level affords unsatisfactory anti-inflammatory effects but, on the other hand, use of higher levels is not preferred for economic reasons.

The lower alkanols used in this invention are, for example, methanol, ethanol, isopropanol and butanol. A preferred amount of the lower alkanol is from about 10% to about 50% by weight of the total.

A preferred amount of water is from about 30% to about 60% by weight of the total.

The lower alkylene glycol having from two to six carbons which can be used includes ethylene glycol, propylene glycol and butylene glycol. Glycerine or polyethylene glycol having an average molecular weight of from 200 to 2000 can also be used in place of glycol. It is possible to use only one kind of such polyhydric alcohol, but more than one kind may also be used. A preferred amount of the polyhydric alcohol is from about 5% to about 40% by weight of the total. Use of the polyhydric alcohol level greater than 40% is not preferred, since the formulation gives unpleasant feelings such as stickiness after use. Although these polyhydric alcohols are known to dissolve active ingredients in bases, it is a particularly surprising feature of this invention that the polyhydric alcohols in combination wit the above-mentioned alkanolamines prevent the conversion of piroxicam into its hydrate, thereby precluding the formation of the previously-mentioned yellow deposit on the skin.

As Table 1 below indicates, it will be understood that when the polyhydric alcohols are not present in the composition, piroxicam crystallizes out as a yellow deposit on the skin:

TABLE 1

Formulation of Yellow Deposit (piroxicam hydrate)

| Formulation | A | B | C | D |
|---|---|---|---|---|
| Polyhydric alcohol | Polyethylene glycol | Polyethylene glycol | Polyethylene glycol and propylene glycol | None |
| Concn. level | 20 w/w % | 30 w/w % | 25 w/w % | |
| Yellow deposit | No | No | No | Yes |

This invention employs a solubilizing agent to dissolve piroxicam in bases for formulation; the piroxicam-solubilizing agent is selected from the class of alkanolamines. It has been discovered that monoalkanolamine, dialkanolamine and trialkanolamine are highly effective for increasing the solubility of piroxicam in the composition, as well as enhancing the skin-permeability of piroxicam. The monoalkanolamines have from one to four carbon atoms and include methanolamine, ethanolamine, propanolamine and butanolamine. The dialkanolamines have from two to eight carbon atoms and include dimethanolamine, diethanolamine, dipropanolamine and dibutanolamine. The trialkanolamines have from three to twelve carbon atoms and include trimethanolamine, triethanolamine, tripropanolamine and tributanolamine.

The marked solubilizing power of these alkanolamines has been demonstrated by reference to testing results where the ability of these amines to dissolve piroxicam is compared with that of other solubilizers listed in the table below (Table 2):

TABLE 2

Piroxicam Solubilizers

| Solubilizers | Amount added | solvent: water Solubility of Piroxicam (mg./g.) |
|---|---|---|
| Ethanolamine | 10% | 392 |
| Diethanolamine | " | 204 |
| Di-isopropanolamine | " | 195 |
| Di-isopropyl adipate | " | 1.2* |
| Diethyl sebacate | " | 2.0* |
| N—Ethyl-o-crotonotoluidide | " | 1.8* |
| Isopropyl myristate | " | 0.4* |
| Ammonia | " | 60.0 |
| Control (none) | 0 | 0.01 |

*solvent: 1:1 water-ethanol

It is possible to use only one kind of the alkanolamines, but more than one kind may also be used. A preferred amount of the alkanolamines is up to about 3% by weight of the total: this amount is sufficient to dissolve piroxicam in the ointment bases, but levels of the alkanolamines are not limited to this range.

In accordance with this invention, carboxyvinyl polymers are used as gel-forming agents. Carboxyvinyl polymers are hydrophillic polymers and prepared by polymerizing monomers principally consisting of acrylic acid. They are commercially available from Goodrich Chemicals, U.S.A., under the trade name of Carbopol 934,940 or 941 and also from Wako Pure Chemicals, Japan under the trade name of HIVIS-WAKO 103, 104 or 105.

An aqueous solution containing the carboxyvinyl polymer is acidic, since the polymer has free carboxylic acid residues. Neutralization of the aqueous solution with an appropriate base furnishes a viscous gel with desired viscosity. The appropriate bases which can be used are the aforementioned alkanolamines, inorganic bases such as sodium hydroxide, potassium hydroxide and potassium carbonate and organic bases such as alkylamine, dialkylamine and trialkylamine. A preferred amount of the gel-forming agent is from about 0.2% to about 2.0% by weight of the total.

A gel ointment formulation containing carboxyvinyl polymer is generally stable. It has a constant viscosity with very little variation due to temperature or time. However, as previously described herein, several problems arise when the compositions of this invention containing carboxyvinyl polymer are applied to the skin. It sometimes happens that the polymer is salted out by the salt contained in sweat and forms soft agglomerates which disintegrate easily. In such a case, the active ingredient may be lost before it is absorbed through skin and the formulation affords an unpleasant feeling on administration.

Accordingly, the formulation must be administered after the area of application is wiped and cleaned. It has been discovered that if certain hydrophilic polymers are incorporated in the formulation, the ointment can be administered topically even on the sweating skin to form a suitable film without the above problems.

Japanese Published Patent Application No. 55-40,604 describes a similar phenomenon and teaches a method for preventing the same with the use of hydroxypropyl cellulose. Hydroxypropyl cellulose has, however, turned out to be ineffective when combined with the compositions of this invention. For the purpose of this invention, polyvinylpyrrolidone, carboxymethyl cellulose and hydroxyethyl cellulose are satisfactory. The film-forming ability of these hydrophilic polymers has been illustrated in the test results of Table 3, as shown below, where the use of film-forming polymers in the compositions of this invention are observed to afford very favorable effects:

TABLE 3

Film-forming Ability of Piroxicam Ointment[1]

| Film-forming agent | Applied to the normal skin | Applied to the skin with brine |
|---|---|---|
| Polyvinylpyrrolidone (1.0% added) | good film | good film |
| Carboxymethyl cellulose (1.0% added) | " | " |
| Hydroxyethyl cellulose (1.0% added) | " | " |
| Hydroxethyl cellulose (0.5% added) | " | " |
| Control (None) | a small amount of soft agglomerates | soft agglomerates disintegrate |

[1]The above formulation contains the following ingredients (Table 4):

TABLE 4

Piroxicam Ointment (1%)

| Ingredient | Percent by weight |
|---|---|
| Piroxicam | 1.0 |
| Carboxyvinyl polymer 940 | 1.0 |
| Ethanol | 30.0 |
| Propylene glycol | 20.0 |
| Ethylene glycol | 10.0 |
| Diethanolamine | 1.5 |
| Distilled water | remaining part |

It is possible to use only one kind of the film-forming agents, but more than one kind may also be used. A preferred amount of the film-forming agents is from about 0.2% to about 2.0% by weight of the total.

In addition to the above-mentioned film-forming agents, various other ingredients can be incorporated into the anti-inflammatory compositions of this invention to improve their therapeutic efficacy and stability. These include antiseptics such as benzyl alcohol, corneous tissue-dissolving agents such as urea and suitable skin-permeation enhancing adjuvants, like diethyl sebecate, etc., which are well-known to those skilled in the art.

The anti-inflammatory compositions of this invention have a pH range of from about 6.5 to about 9.0, and preferably from 6.5 to 8.0. In general, it is believed that the percutaneous absorption or skin-penetration of a given drug is dependent upon the ratio of lipophilicity to water solubility (partition coefficient) and that a high ratio is preferred, but too high a ratio adversely decreases the absorption and skin-penetration. Piroxicam has a pKa value of from 1.5 to 5.1. A preferred pH range for the compositions of this invention is from about 6.5 to about 8.0, since it is in this range that piroxicam is present partially in a dissociated form and the alkanolamines can also be used. At a higher pH than 9.0, piroxicam is chemically unstable and may even decompose or deteriorate in quality.

Accordingly, the compositions of this invention can be prepared in the manner described below:

1. dispersing carboxyvinyl polymer and, if desired, a film-forming agent in distilled water;
2. blending the above with lower alkanols, glycols, glycerine or polyethlene glycols uniformly;
3. independently dissolving piroxicam in an aqueous solution of alkanolamine until it is completely dissolved and, if necessary, adding a neutralizing agent thereto; and
4. adding the resulting mixture of step 3 to the mixture obtained in step 2 and mixing under constant agitation to form a gel ointment.

The compositions of this invention so produced are stable even after storage for a prolonged period of time and exhibit excellent anti-inflammatory activity, as is evident from the following examples. These examples further illustrate this invention, but are not to be construed as limiting the same.

EXAMPLE 1

The following ingredients were combined and blended uniformly together to produce an ointment formulation having a pH of 7.9:

| | Percent by weight |
|---|---|
| Piroxicam | 1.0 |
| Carboxyvinyl polymer 940 | 1.0 |
| Ethanol | 30.0 |
| Propylene glycol | 30.0 |
| Diethanolamine | 1.5 |
| Hydroxyethyl cellulose | 0.5 |
| Polyvinylpyrrolidone K-30 | 0.5 |
| Distilled water | remaining part |

EXAMPLE 2

The following ingredients were combined and blended uniformly together to produce an ointment formulation having a pH of 7.8:

| | Percent by weight |
|---|---|
| Piroxicam | 1.0 |
| Carboxyvinyl polymer 940 | 1.0 |
| Ethanol | 30.0 |
| Glycerine | 20.0 |
| Polyethylene glycol 300 | 10.0 |
| Diisopropanolamine | 1.7 |
| Distilled water | remaining part |

EXAMPLE 3

The following ingredients were combined and blended uniformly together produce an ointment formulation having a pH of 8.0:

| | Percent by weight |
|---|---|
| Piroxicam | 1.0 |
| Carboxyvinyl polymer 940 | 1.0 |
| Ethanol | 30.0 |
| Propylene glycol | 10.0 |
| Glycerine | 10.0 |
| Diisopropanolamine | 1.8 |
| Hydroxyethyl cellulose | 1.0 |
| Distilled water | remaining part |

EXAMPLE 4

The following ingredients were combined and blended uniformly together to produce an ointment formulation having a pH of 7.3:

| | Percent by weight |
|---|---|
| Piroxicam | 1.0 |
| Carboxyvinyl polymer 940 | 1.0 |

|  | Percent by weight |
| --- | --- |
| Ethanol | 30.0 |
| Glycerine | 30.0 |
| Diethanolamine | 1.3 |
| Distilled water | remaining part |

EXAMPLE 5

The following ingredients were combined and blended uniformly together to produce an ointment formulation having a pH of 7.7:

|  | Percent by weight |
| --- | --- |
| Piroxicam | 1.0 |
| Carboxyvinyl polymer 940 | 1.0 |
| Ethanol | 30.0 |
| Propylene glycol | 10.0 |
| Polyethylene glycol 300 | 10.0 |
| Diethanolamine | 1.7 |
| Carboxymethyl cellulose | 1.0 |
| Distilled water | remaining part |

EXAMPLE 6

The following ingredients were combined and blended uniformly together to produce an ointment formulation having a pH of 8.2:

|  | Percent by weight |
| --- | --- |
| Piroxicam | 1.0 |
| Carboxyvinyl polymer 940 | 1.0 |
| Ethanol | 30.0 |
| Glycerine | 20.0 |
| Diethanolamine | 1.3 |
| Triethylamine | q.s. |
| Hydroxethyl cellulose | 0.5 |
| Distilled water | remaining part |

EXAMPLE 7

The following ingredients were combined and blended uniformly together to produce an ointment formulation having a pH of 7.6:

|  | Percent by weight |
| --- | --- |
| Piroxicam | 1.0 |
| Carboxyvinyl polymer 940 | 0.7 |
| Ethanol | 35.0 |
| Propylene glycol | 20.0 |
| Polyethylene glycol 300 | 10.0 |
| Diisopropanolamine | 1.5 |
| Distilled water | remaining part |

EXAMPLE 8

The following ingredients were combined and blended uniformly together to produce an ointment formulation having a pH of 6.7:

|  | Percent by weight |
| --- | --- |
| Piroxicam | 1.0 |
| Carboxyvinyl polymer 940 | 1.0 |
| Ethanol | 40.0 |
| Polyethylene glycol 300 | 20.0 |
| Diisopropanolamine | 1.0 |
| Triethylamine | q.s. |
| Distilled water | remaining part |

EXAMPLE 9

The following ingredients were combined and blended uniformly together to produce an ointment formulation having a pH of 7.7:

|  | Percent by weight |
| --- | --- |
| Piroxicam | 0.5 |
| Carboxyvinyl polymer 940 | 0.7 |
| Ethanol | 25.0 |
| Propylene glycol | 20.0 |
| Benzyl alcohol | 1.0 |
| Hydroxyethyl cellulose | 0.4 |
| Diisopropanolamine | 1.2 |
| Water | 51.2 |

EXAMPLE 10

The following ingredients were combined and blended uniformly together to produce an ointment formulation having a pH of 7.8:

|  | Percent by weight |
| --- | --- |
| Piroxicam | 1.0 |
| Carboxyvinyl polymer 940 | 0.9 |
| Ethanol | 30.0 |
| Propylene glycol | 7.5 |
| Polyethylene glycol 300 | 7.5 |
| Benzyl alcohol | 1.0 |
| Hydroxyethyl cellulose | 0.5 |
| Diisopropanolamine | 1.7 |
| Water | 49.9 |

EXAMPLE 11

Analgesic Testing

Piroxicam ointment (1%), prepared according to Example 10, at a dose level of 100 mg. per mouse was administered topically to a group of ten mice on the paw of their hind legs in order to determine the effects of the compositions of this invention on adjuvant induced pain in the joints. Pain threshold values were measured five hours later by means of an Analgesymeter (UGO BASILE) and the results obtained are shown below in the following table (Table 5):

TABLE 5

|  | Pain threshold value (g) | |
| --- | --- | --- |
| Drug | Before administration | Five hours after |
| Control (non-drug) | 46.7 ± 3.3 | 46.7 ± 2.0 |
| 1% Piroxicam ointment | 42.2 ± 3.2 | 105.6 ± 17.5 |

The above test results indicate that the compositions of this invention are active analgesics against adjuvant induced joint pain.

EXAMPLE 12

Anti-inflammatory Activity

The anti-inflammatory activity of the compositions of this invention was determined using the standard carragenin-induced rat foot edema test. [C. A. Winter et al., *Proceedings of the Society for Experimental Biology and Medicine,* Vol. 111, p. 544 (1962)]. Piroxicam ointment (1%), prepared according to Example 10, was administered topically at a dose level of 100 mg. per rat. The results obtained are presented in the table below (Table 6) in terms of the percent inhibition of edema formation, as compared to the non-drug treated control and the oral administration of piroxicam (1 mg./kg.):

TABLE 6

| Drug | % Inhibition of edema |
| --- | --- |
| 1% Piroxicam ointment | 41.6 |
| Oral administration | 39.6 |
| Control | — |

The above test results indicate that the compositions of this invention inhibit the edema formation significantly and they are as effective as the oral route of piroxicam administration.

What is claimed is:

1. A topical anti-inflammatory composition in gel ointment form comprising in an aqueous system an effective anti-inflammatory amount of piroxicam; from about 10% to about 50% by weight of a lower alkanol having from one to four carbon atoms; from about 0.2% to about 2.0% by weight of carboxyvinyl polymer; from about 5% to about 40% by weight of at least one polyhydric alcohol selected from the group consisting of lower alkylene glycol having from two to six carbon atoms, glycerine and polyethylene glycol having an average molcular weight of 200 to 2,000; and a piroxicam-solubilizing amount of from about 1.0% to about 3.0% by weight of at least one alkanolamine having from one to four carbon atoms, dialkanolamine having from two to eight carbon atoms and trialkanolamine having from three to twelve carbon atoms; and from about 0.2% by weight to about 2.0% by weight of at least one film-forming agent selected from the group consisting of carboxymethyl cellulose, hydroxyethyl cellulose and polyvinylpyrrolidone, and sufficient water to total 100%, said composition having a pH range of from about 6.5 to about 9.0.

2. A composition as claimed in claim 1 wherein piroxicam is present at a concentration level of from about 0.3% to about 2.0% by weight of the total.

3. A composition as claimed in claim 1 wherein water is present at a concentration level of from about 30% to about 60% by weight of the total.

4. A topical anti-inflammatory composition in gel ointment form comprising from about 0.3% to about 2.0% by weight of piroxicam; from about 30% to about 60% by weight of water; from about 10% to about 50% by weight of a lower alkanol having from one to four carbon atoms; from about 0.2% to about 2.0% by weight of carboxyvinyl polymer; from about 5% to about 40% by weight of at least one polyhydric alcohol selected from the group consisting of lower alkylene glycol having from two to six carbon atoms, glycerine and polyethylene glycol having an average molecular weight of from 200 to 2,000; and a piroxicam-solubilizing amount of from about 1.0% to about 3.0% by weight of at least one alkanolamine selected from the group consisting of monoalkanolamine having from one to four carbon atoms, dialkanolamine having from two to eight carbon atoms and trialkanolamine having from three to twelve carbon atoms; and from about 0.2% to about 2.0% by weight of at least one film-forming agent selected from the group consisting of carboxymethyl cellulose, hydroxyethyl cellulose and polyvinylpyrrolidone, said composition having a pH range of from about 6.5 to about 9.0.

* * * * *